United States Patent
Carrier et al.

(10) Patent No.: US 8,367,340 B2
(45) Date of Patent: Feb. 5, 2013

(54) PROGNOSTIC TOOLS TO PREDICT THE EFFICACY OF DRUG TREATMENT TARGETING CHROMATIN DNA OR ENZYMES ACTING ON DNA

(75) Inventors: France Carrier, Silver Spring, MD (US); Narasimharoa Nalabothula, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 281 days.

(21) Appl. No.: 12/630,022

(22) Filed: Dec. 3, 2009

(65) Prior Publication Data

US 2010/0173301 A1 Jul. 8, 2010

Related U.S. Application Data

(60) Provisional application No. 61/119,498, filed on Dec. 3, 2008.

(51) Int. Cl.
*C12Q 1/68* (2006.01)
*C12P 19/34* (2006.01)

(52) U.S. Cl. .................. 435/6.12; 435/6.1; 435/6.11

(58) Field of Classification Search .............. None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,889,818 A | 12/1989 | Gelfand et al. |
| 5,038,852 A | 8/1991 | Johnson et al. |
| 5,994,056 A | 11/1999 | Higuchi |
| 6,171,785 B1 | 1/2001 | Higuchi |
| 7,312,054 B2 | 12/2007 | Mautner |

OTHER PUBLICATIONS

Fernando et al., "Quantitation of Gene-Specific DNA Damage by Competitive PCR," Analytical Biochemistry, 2002, vol. 306, pp. 212-221.*

Ponchel et al., "Real-time PCR based on SYBR-Green I fluorescence: An alternative to the TaqMan assay for a relative quantification of gene rearrangements, gene amplifications and micro gene deletions," BMC Biotechnology, 2003, vol. 3, pp. 1-13.*

Dolganov et al., "A Novel Method of Gene Trasncript Profiling in Airway Biopsy Homogenates Reveals Increased Expression of a Na+—K+—Cl- Cotransporter (NKCC1) in Asthmatic Subjects," Genome Research, 2001, vol. 11, pp. 1473-1483.*

Kim, et al., (2003) "Inhibition of histone deacetylase increases cytotoxicity to anticancer drugs targeting DNA." Cancer Res, 63, 7291-300.

Jennerwein, et al., (1991) "A polymerase chain reaction-based method to detect cisplatin adducts in specific genes." Nucleic Acids Res, 19, 6209-14.

Grimaldi, et al. (1994) "DNA damage by anticancer agents and its repair: mapping in cells at the subgene level with quantitative polymerase chain reaction." Anal Biochem, 222, 236-42.

Oshita, et al., (1994) "Rapid polymerase chain reaction assay to detect variation in the extent of gene-specific damage between cisplatin- or VP-16-resistant and sensitive lung cancer cell lines." Jpn J Cancer Res, 85, 669-73.

Maniatis et al., Molecular Cloning: A Laboratory Manual (New York, Cold Spring Harbor Laboratory, 1989).

Arrand, Preparation of Nucleic Acid Probes, in pp. 18-30, Nucleic Acid Hybridization: A Practical Approach (Ed Hames and Higgins, IRL Press, 1985).

PCR Protocols. Chapters 18-20 (Innis et al., ed., Academic Press, 1990).

Gewirtz et al., (1998) "Induction of DNA damage, inhibition of DNA synthesis and suppression of c-myc expression by the anthracycline analog, idarubicin (4-demethoxy-daunorubicin) in the MCF-7 breast tumor cell line." Cancer Chemother Pharmacol, 41, 361-9.

Schmittgen et al., (2008) "Analyzing real-time PCR data by the comparative C(t) method." Nat Protoc, 3, 1101-8.

Poster-Dubai, UAE, Feb. 2008.

Poster, SanDiego, California, Apr. 13, 2008.

Shanghai, China Presentation, Jun. 12, 2008.

* cited by examiner

*Primary Examiner* — Young J Kim (74) *Attorney, Agent, or Firm* — Castellano PLLC (57) ABSTRACT

Disclosed are methods of predicting cell response to drug-based therapy using both PCR-Stop assays and real time PCR assays. Methods herein may be used for assessment of drug effect, evaluation of regimen suitability for a given patient, and/or for determination of an optimal drug dose. Also provided are isolated oligonucleotide primers such as primers capable of annealing under PCR conditions to a segment of a c-myc locus, where the primers may be used in the disclosed methods. Further disclosed are kits and systems that may be used for predicting a cell response to drug-based therapy.

8 Claims, 6 Drawing Sheets

PROGNOSTIC TOOLS TO PREDICT THE EFFICACY OF DRUG TREATMENT TARGETING CHROMATIN DNA OR ENZYMES ACTING ON DNA

RELATED APPLICATION

This application claims the benefit of U.S. Provisional Application No. 61/119,498 filed on Dec. 3, 2008, the entire contents of which are hereby incorporated by reference in their entirety.

STATEMENT REGARDING FEDERALLY SPONSORED RESEARCH

This invention was made with government support under Grant Number CA116491 awarded by the National Institutes of Health. The government has certain rights in the invention.

FIELD

The present embodiments relate generally to methods of predicting a response of cells to drug-based therapy using PCR-Stop assays followed by real time PCR. Non-limiting example embodiments may include predicting cell response to at least one drug. According to non-limiting example embodiments, the at least one drug may include a combination therapy of at least one HDACi followed by at least one anticancer drug, where HDACis facilitate chromatin accessibility at specific loci targeted by anticancer drugs for example in human cancer cells. The present embodiments are not limited however, to cancer cells or human cells. Any cells containing DNA could be tested in accordance with the present methods.

Also provided are isolated oligonucleotide primers provided herein, including for example, primers capable of annealing under PCR conditions to a segment of a c-myc locus.

Further provided are kits and systems for predicting cell response to drug-based therapy.

SEQUENCE LISTING

The instant application contains a Sequence Listing which has been submitted via EFS-Web and is hereby incorporated by reference in its entirety. Said ASCII copy, created on Mar. 2, 2010, is named 12630022.txt, and is 1,283 bytes in size.

BACKGROUND

Chemotherapy is widely used to eliminate cancerous cells. Some chemo-therapeutic agents kill a cell during any phase of the cycle (these are called cell-cycle non-specific), others kill during a specific phase and are unable to work on the resting phase cells (called cell-cycle specific). However, a combination of specific and non-specific chemotherapeutics has been shown as a better chemotherapeutic strategy in certain circumstances. Most chemotherapeutic regimens include at least one drug targeting DNA or an enzyme acting on DNA. Drugs that have been known to target the S phase of the cell cycle, most effectively, include for example, cross-linking agents such as cisplatin and its derivatives and small molecule inhibitors of topoisomerases.

Topoisomerases are a group of enzymes that control the juxtaposed intra molecular stress in DNA due to replication or transcription, by catalyzing the breaking and rejoining of the phosphodiester backbone. Type I topoisomerases change DNA linking number by cutting one strand of a DNA double helix and then rejoining the cut strand. On the other hand, type II topoisomerases relax supercoiled DNA by cutting both strands of DNA double helix, followed by passing DNA strands through it, and then re-annealing the cut strands. Type I topoisomerase makes single-stranded nicks to relieve supercoiling that generates during DNA replication and transcription. Type II topoisomerase act as a molecular motor during the cell cycle, using the energy gained from ATP hydrolysis to introduce tight supercoils into the DNA helix in order to condense the chromosome. Because this process must be highly regulated, type II topoisomerase can form molecular complexes with important cell-cycle regulators (such as p53, TopBP1, 14-3-3 epsilon, and Cdc2) to ensure that chromosome condensation occurs at the correct time in the cell cycle.

Open (relaxed) and closed (condensed) conformations of chromatin occur through acetylation and de-acetylation in eukaryotes. Histone Acetyl Transferase (HAT) mediated acetylation permits chromatin remodeling complexes and transcription factors to access DNA and induce gene expression, respectively. On the contrary, Histone Deacetylases (HDAC) repress gene expression by de-acetylating histone tails which result in chromatin condensation. Earlier studies have shown increased HDAC activity in cancer cells.

SUMMARY

According to non-limiting example embodiments, the present inventors have developed methods that include exposing cells to at least one drug, and performing both a PCR Stop assay and a real time PCR assay to predict the receptiveness of cells to drugs. In accordance with non-limiting example embodiments, the methods may include exposing cancer cells to any anticancer drugs. By way of further example, the methods may include exposing cancer cells to a combination of HDAC inhibitors (HDACi) followed by topoisomerase inhibitors. The present inventors' studies have shown that the treatment of HDACi followed by topoisomerase inhibitors or other anticancer drugs increased the cancer cell killing efficiency by several fold. (Kim, M. S., Blake, M., Baek, J. H., Kohlhagen, G., Pommier, Y. and Carrier, F. (2003) "Inhibition of histone deacetylase increases cytotoxicity to anticancer drugs targeting DNA." *Cancer Res*, 63, 7291-300.)

Non-limiting example embodiments are directed to methods of predicting a response to drug-based therapy that include exposing cells to at least one drug; and measuring an amount of amplified product accumulated after a PCR-stop assay is performed on the cells, where the amount of amplified product is measured using real time PCR, and wherein the amount of amplified product is inversely proportional to incidence of DNA breaks in an amplified region. The cell response to the at least one drug may be quantified based on the incidence of DNA breaks determined from the measured amount of amplified product.

Also provided are isolated oligonucleotide primers having about 10-30 nucleotides in length, where isolated oligonucleotide primers are capable of annealing under PCR conditions to a segment of a c-myc locus.

Further provided are systems and kits that include one or more components of a PCR stop assay, one or more components of a real time PCR assay, and one or more components to isolate genomic DNA, which kits and systems may be used for predicting cancer cell response to drug-based therapy.

BRIEF DESCRIPTION OF THE FIGURES

Non-limiting example embodiments described herein, with reference to the following accompanying Figures:

FIG. 2A1 and FIG. 2B1 are stained agarose gels of a PCR-Stop assay performed on genomic DNA obtained from cells (RKO—colon cancer cells in FIG. 2A1, and normal intestinal cells in FIG. 2B2) treated with various drugs. FIG. 2A2 and FIG. 2B2 are Real Time PCR measurements of c-myc P2 promoter expressed as a percentage of untreated samples.

DETAILED DESCRIPTION

Currently there is no diagnostic/prognostic tool capable of predicting a patient's response to a given regimen of anticancer drugs targeting chromatin DNA and/or enzymes acting on chromatin associated DNA. Typically, patients receive the same standard "one-fits-all" approach. Assessments are generally made after-the-fact, which means that patients may undergo therapies for which they are not responsive. This may waste valuable time (and resources) during which the patient could be undergoing other therapies to which they may be responsive. The methods herein may be used to screen which patients may be receptive to certain drug therapies and/or which drug therapies may work on particular patients.

Provided herein are example kits and methods for preclinical and/or clinical assessment of drug effect, evaluation of regimen suitability for a given patient, and determination of optimal drug dose. One of the many advantages of the present methods include being able to assess drug response by quantitating DNA damage at a specific locus. The present methods are also advantageous in reduction of labor time and cost in identifying reliable primers and avoiding radioactive material usage (used in the original PCR stop assay discussed below).

Additional aspects, advantages and/or other features of example embodiments of the invention will become apparent in view of the following detailed description, taken in conjunction with the accompanying drawings. It should be apparent to those skilled in the art that the described embodiments provided herein are merely exemplary and illustrative and not limiting. Numerous embodiments of modifications thereof are contemplated as falling within the scope of this disclosure and equivalents thereto.

All patents and publications mentioned in this specification are indicative of the level of those skilled in the art to which the invention pertains. All patents and publications herein are incorporated by reference to the same extent as if each individual publication was specifically and individually indicated as having been incorporated by reference in its entirety.

In describing example embodiments, specific terminology is employed for the sake of clarity. However, the embodiments are not intended to be limited to this specific terminology. Unless otherwise noted, technical terms are used according to conventional usage.

As used herein, "a" or "an" may mean one or more. As used herein "another" may mean at least a second or more. Furthermore, unless otherwise required by context, singular terms include pluralities and plural terms include the singular.

Non-limiting example embodiments are directed to methods that include exposing cells to at least one drug; isolating genomic DNA from the cells; performing a PCR stop assay on the genomic DNA, thus producing amplified product; and measuring the amount of amplified product using real-time PCR.

Further non-limiting example embodiments include methods of predicting a response to drug-based therapy that include exposing cells, such as cancer cells, to at least one drug; performing a PCR-stop assay on the cells; and quantifying an amount of accumulated PCR amplified product using real time PCR, wherein the amount of PCR amplified product is inversely proportional to incidence of DNA breaks in an amplified region. Cell response to the at least one drug may be assessed based on the incidence of DNA breaks, which can be determined from the measured amount of PCR amplified product.

The methods herein include quantitative assays to measure DNA breaks introduced in genomic DNA (gDNA) due to inhibition of topoisomerase function, at specific locus by combining a PCR-stop assay with real-time PCR. The extent of locus-specific DNA damage sustained by cells when exposed to drugs under study, predicts the response to drug-based therapy.

According to non-limiting example embodiments, the drug-based therapy is drug-based combinatorial chemotherapy to treat cancer cells. For example, according to non-limiting example embodiments, cancer cells are exposed to at least one drug that may include at least one Histone Deacetylase Inhibitor (HDACi) and at least one anticancer drug. Such drug-based combinatorial therapy may include for example, pre-treating a patient (or cells extracted from a patient) with an HDACi to increase the killing efficiency of conventional anticancer drugs. Example methods may include exposing cancer cells to at least one HDACi and thereafter at least one anticancer drug.

According to non-limiting example embodiments, the at least one HDACi may include any type of drugs that may inhibit Histone Deacetylase Activity, such as hydroxamic acid, cyclic peptides, benzamide and short-chain fatty acids. By way of non-limiting example embodiment, the at least one HDACi may include at least one of trichostatin A (TSA), vorinostat (SAHA), sodium butyrate, phenylbutyrate, Valproic acid, Tributyrin, MS-275, CI994, CBHA, Depsipeptide or other suitable derivative that may be developed.

According to non-limiting example embodiments, the at least one drug may include any drugs that can cause DNA breaks. For example, the drug may include at least one anticancer drug targeting DNA or enzymes acting on the DNA. Non-limiting example embodiments may include for example, intra and inter cross-linking agents, Topoisomerase 1 inhibitors, Topoisomerase 2 inhibitors, alkylating agents, and antimetabolites. Non-limiting example embodiments of anticancer drugs may include etoposide (VP-16), Ara-C, ellipticine, doxorubicin, and cisplatin.

According to non-limiting example embodiments, cells may be exposed to the at least one drug, while the cells are in a patient, and then the cells may be removed from the patient prior to performing the PCR-Stop in Real Time assays. According to alternative embodiments, cells may be removed from a patient before being exposed to at least one drug. The latter embodiments may be advantageous in avoiding exposing a patient to drugs that may not be effective in treating his/her particular cancer cells. The former embodiments may be advantageous for example, in quantitatively assessing whether current treatments are working/effective at treating the cells.

A purpose of the present methods is to test various cells for potential response to various therapies. Cells may include for example, any cells containing DNA that can be tested according to the present methods. Therefore, it is contemplated that numerous, various cells, such as cancer cells may be subjected to the present methods. Example cells may include any cancer cells that can be biopsied and hematopoetic cancer cells. Cancer cells that may be subjected to the present methods may include, but are not limited to the following: RKO (colon cancer) cells, MCF-7 (breast cancer) cells, U118 (glioblastoma) cells, and D54 (brain cancer) cells.

PCR-stop assays were originally described to assess the amount of DNA strand breaks generated by anticancer drugs in vitro. (See Jennerwein, M. M. and Eastman, A. (1991) "A polymerase chain reaction-based method to detect cisplatin adducts in specific genes." *Nucleic Acids Res*, 19, 6209-14; Grimaldi, K. A., Bingham, J. P., Souhami, R. L. and Hartley, J. A. (1994) "DNA damage by anticancer agents and its repair: mapping in cells at the subgene level with quantitative polymerase chain reaction." *Anal Biochem*, 222, 236-42; and Oshita, F. and Saijo, N. (1994) "Rapid polymerase chain reaction assay to detect variation in the extent of gene-specific damage between cisplatin- or VP-16-resistant and sensitive lung cancer cell lines." *Jpn J Cancer Res*, 85, 669-73). The PCR-stop method has never been used however, to evaluate cancer patients' cells response to combinatorial chemotherapeutic drugs. Moreover, in the original PCR stop assay technique, radioactive nucleotides were used to detect the amount of DNA breaks and use of radioactive material can be a challenging problem. Sensitivity of the technique has never been good enough to detect DNA damage response to low drug doses. Reproducibility was also a serious problem due to the choice of PCR primers. Thus, the technique has never been developed into a reliable and well accepted technique. A PCR-Stop assay has also never been used in combination with real-time PCR (RT-PCR) for assessment of anti-cancer drug efficiency.

According to non-limiting example methods, a PCR-stop assay may be carried out on genomic DNA isolated from cells that are either untreated or treated with drugs under study. A variety of techniques for extracting nucleic acids from biological samples are known in the art. For example, see those described in Maniatis et al., Molecular Cloning: A Laboratory Manual (New York, Cold Spring Harbor Laboratory, 1982); Arrand, Preparation of Nucleic Acid Probes, in pp. 18-30, Nucleic Acid Hybridization: A Practical Approach (Ed Hames and Higgins, IRL Press, 1985); or, in PCR Protocols. Chapters 18-20 (Innis et al., ed., Academic Press, 1990).

Figure 1:
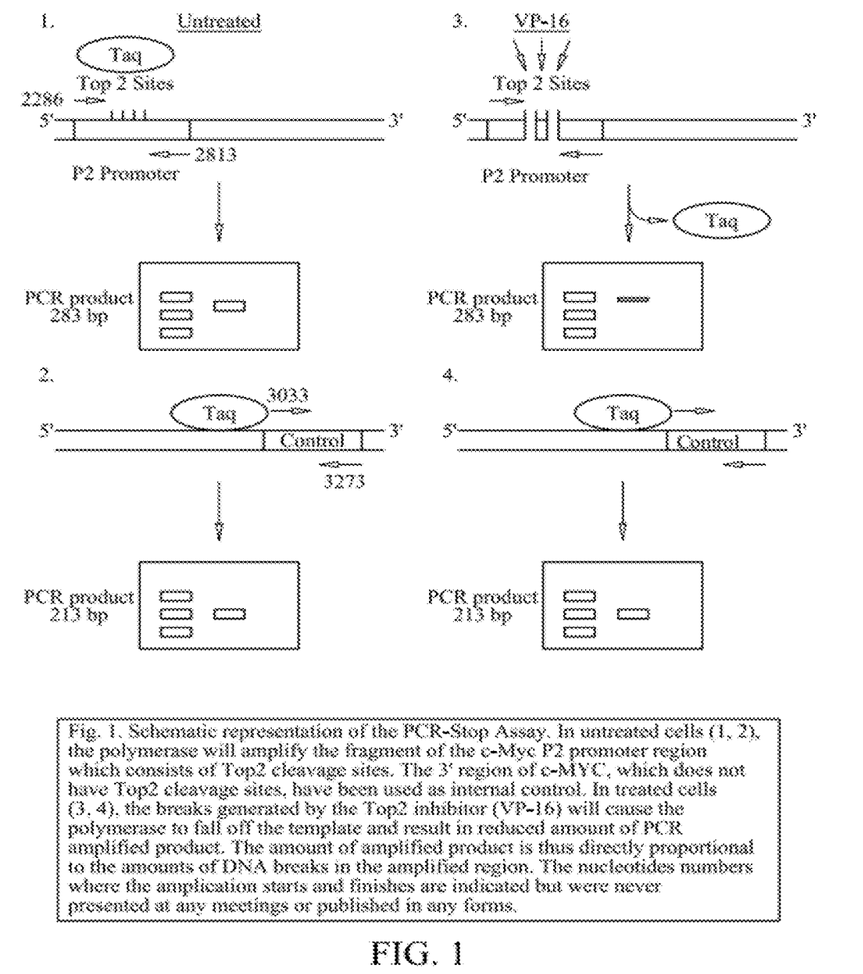
FIG. 1 is a schematic representation of a PCR-Stop Assay in accordance with non-limiting example embodiments.

In a PCR-stop assay in accordance with the present methods, DNA polymerase stops DNA replication whenever it encounters a break that is introduced within the amplification region. FIG. 1 is a schematic representation of a PCR Stop Assay in accordance herewith. In particular, FIG. 1 depicts a non-limiting example of a combinatorial assay in accordance with example methods.

Amplification of DNA by PCR is disclosed in U.S. Pat. Nos. 4,683,195 and 4,683,202 (both of which are incorporated herein by reference). Generally, PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so that DNA synthesis by the polymerase proceeds across the region between the primers, effectively doubling the amount of the DNA segment. Moreover, because the extension products are also complementary to and capable of binding primers, each successive cycle essentially doubles the amount of DNA synthesized in the previous cycle. This results in the exponential accumulation of the specific target fragment, at a rate of approximately 2 n per cycle, where n is the number of cycles.

According to non-limiting example embodiments Taq DNA polymerase may be used in the PCR-Stop assay (See e.g., FIG. 1). Taq polymerase, a thermostable polymerase, is active at high temperatures. Methods for the preparation of Taq are disclosed e.g., in U.S. Pat. No. 4,889,818, which is incorporated herein by reference. Other thermostable DNA polymerases can also be used in PCR as would be known to those skilled in the art. One can use any enzyme that amplifies DNA in a PCR reaction.

As used herein, the term "primer" refers to an oligonucleotide capable of acting as a point of initiation of DNA synthesis when annealed to a nucleic acid template under conditions in which synthesis of a primer extension product is initiated, i.e., in the presence of nucleotide triphosphates and a DNA polymerase in an appropriate buffer ("buffer" includes pH, ionic strength, cofactors, etc.) and at a suitable temperature. Suitable PCR conditions including annealing temperature and time may be determined by those skilled in the art.

The primer must be sufficiently long to prime the synthesis of extension products in the presence of the agent for polymerization, which may contain for example, 10-30 nucleotides or 10-25 nucleotides. Short primer molecules generally require cooler temperatures to form sufficiently stable hybrid complexes with the template.

As shown in FIG. 1, in untreated cells (FIG. 1(1) and FIG. 1(2)), the polymerase will amplify the fragment of the c-myc P2 promoter region, which includes Top2 cleavage sites. Top2 inhibitors induce preferential damage within the c-myc locus and more particularly within the P2 promoter of c-myc. The 3' region of c-myc, which does not have Top2 cleavage sites, has been used as an internal control. By way of non-limiting example, the 3' end region may be amplified using the following primers of the human c-myc gene: Forward: 5'CCCTTTATAATGCGAGGGTCT3' [SEQ ID NO: 1], Reverse: 5'GGCTAGGGTGGAAGAGCC3' [SEQ ID NO:2]. Other suitable primers may be used, as would be apparent to those skilled in the art.

By way of non-limiting example, the following c-myc locus sequence that has not been used before, may be targeted: CCCTTTATAATGCGAGGGTCTGG<ACGGCT GAGGACCCCCGAGCTGTGCTGCTCGCGGCCGCCA CCGCCGGGCCCCGGCCGTCCCTGGCTCCCCT CCTG CCT><CGAGAAGGGCAGGGCTTCTCAGAGGCTTGG CGGGAAAAAGAACGGAGGGAGGGATCGCGCTGAG TATAAAAGCCGGTTTTCGGGGCTTTATCTAACTCGC TGTAGTAATTCCAGCGAGAGGCAGAGGGAGCGAG CGGG CGG>CCGGCTAGGGTGGAAGAGCC. [SEQ ID NO: 3]. Any region of DNA that has topoisomerase II or cross linking agent targeted sites (c-myc locus) or topoisomerase I sites (Hsp-70 locus) can be targeted.

Primers used in the present methods may be selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer.

The oligonucleotide primers may be prepared using any suitable method, such as, for example, the phosphotriester and phosphodiester methods, or automated embodiments thereof, as would be apparent to those skilled in the art. It is also possible to use a primer that has been isolated from a biological source (such as a restriction endonuclease digest).

Further non-limiting example methods of predicting a response to drug-based therapy include exposing cancer cells to at least one drug; mixing (i) DNA extracted from the cancer cells and (ii) a primer pair that includes a forward primer and a reverse primer that target a c-myc promoter sequence; amplifying DNA in a PCR Stop reaction, under conditions to allow production of an amplicon; and quantifying an amount of accumulated PCR amplified product.

In drug treated cells (see e.g., FIG. 1(3) and FIG. 1(4)), the breaks generated by the Top2 inhibitor (in this case VP-16), may cause the polymerase to fall off the template and result in reduced amount of PCR amplified product. VP-16 (etoposide) was selected as an example Type II topoisomerase poison for FIG. 1, because VP-16 and Doxorubicin have induced prominent type II topoisomerase mediated cleavage in the P2 promoter of the c-myc gene. (Gewirtz, D. A., Randolph, J. K., Chawla, J., Orr, M. S. and Fornari, F. A. (1998) "Induction of DNA damage, inhibition of DNA synthesis and suppression of c-myc expression by the anthracycline analog, idarubicin (4-demethoxy-daunorubicin) in the MCF-7 breast tumor cell line." *Cancer Chemother Pharmacol*, 41, 361-9). Those skilled in the art would recognize that alternative embodiments may include ellipticin, doxorubicin, Ara-C or cisplatin as example anti-cancer drugs.

The present methods include quantifying or measuring the PCR amplified product from the PCR Stop assay. According to example embodiments, the amount of PCR amplified product may be measured or quantified using real time PCR methods. The amount of PCR amplified product is inversely proportional to the amounts of DNA breaks in the amplified region. That is, the amount of product accumulated after 'n' number of PCR cycles (as can be determined using Real time PCR) is inversely proportional to the incidence of DNA breaks in the amplified region. Therefore, one can determine the approximate incidence of DNA breaks in the amplified region after measuring or quantifying the amount of PCR amplified product. The higher the incidence of DNA breaks, the greater the efficacy of the given drugs.

Real-time PCR automates an otherwise difficult quantitation process by quantitating reaction products for each sample in every cycle. Data analysis, including copy number calculation, is performed automatically. Currently four different chemistries, TaqMan® (Applied Biosystems, Foster City, Calif., USA), Molecular Beacons, Scorpions® and SYBR® Green (Molecular Probes), are available for real-time PCR. (See RT-PCR: The Basics, by Subbu Dharmaraj, MS—Applied Biosystems). All of these methods allow detection of PCR products via the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moiety to the same or different oligonucleotide substrates.

According to example embodiments, real time PCR methods that may be used in accordance with the present methods may include using SYBR® Green Fluorescence. The SYBR® Green Dye is a nucleic acid stain that binds double-stranded DNA molecules, emitting a fluorescent signal on binding. SYBR® Green is a fluorogenic dye that exhibits little fluorescence when in solution, but emits a strong fluorescent signal upon binding to double-stranded DNA. In particular, SYBR® Green binds double-stranded DNA, and upon excitation emits light. Thus, as a PCR product accumulates, fluorescence increases. SYBR®Green provides a relatively simple format for detecting and quantitating PCR products in real-time reactions. (See Dharmaraj).

SYBR® Green is an economical choice for real-time PCR product detection. Because the dye binds to double-stranded DNA, there is no need to design a probe for any particular target being analyzed. However, detection by SYBR® Green requires optimization. Because the dye cannot distinguish between specific and non-specific product accumulated during PCR the method has been validated and optimized as described.

According to example embodiments, a comparative threshold ($C_t$) method may be used to quantify the results obtained by the real-time RT-PCR. The comparative $C_t$ method involves comparing the $C_t$ values of the samples of interest with a control or calibrator such as a non-treated sample from normal tissue. The $C_t$ values of both the calibrator and the samples of interest are normalized to an appropriate endogenous housekeeping gene. Non-limiting example quantification methods include identifying the cycle number at which the reporter dye emission intensities rises above background noise: this cycle number is called the threshold number ($C_t$). The $C_t$ is proportional to the breaks introduced in the target template; the higher the amount of breakage in the given target template, the higher the $C_t$ measured.

By way of non-limiting example, the 3' region of c-myc gene that has no type II topoisomerase cleavage site may be used as a reference. $C_t$ values of reference (3' region of c-myc gene) as well as test (P2 promoter of c-myc locus) samples were subjected to LIVAK method (see Schmittgen, T. D. and Livak, K. J. (2008) "Analyzing real-time PCR data by the comparative C(t) method." *Nat Protoc*, 3, 1101-8) to calculate the fraction of DNA breaks present in gDNA from drug-treated cells compared to gDNA from untreated cells.

Use of the threshold concentration ($C_t$) for determining quantification of DNA breaks at specific locus is a reason why the present methods are more reliable than the original PCR-Stop assay. According to non-limiting example embodiments of methods herein, the PCR amplified product is quantified by identifying the cycle number at which reporter dye emission intensities rise above background noise, where the higher the cycle number, the higher the amount of DNA breaks. According to these embodiments, the reporter dye may include an SYBR® green dye. High specificity of this method may be conferred by the requirement of oligonucleotides that would give a single band with high PCR efficiency.

As an alternative to the Comparative threshold method, it is contemplated that a Standard Curve method may be used to quantify the results obtained by the real-time RT-PCR. For example, the standard curve method can also be used with isolated DNA containing the P1 and P2 promoter sequence of c-myc locus.

The present inventors have also designed sets of highly specific primers that can be used efficiently and reliably in the present methods. By way of non-limiting example, the present inventors have designed a forward primer complimentary to the upstream sequence of type II topoisomerase site and a reverse primer complimentary to the downstream sequence of type II topoisomerase site in the c-myc locus.

Non-limiting example embodiments include isolated oligonucleotide primers of about 10-30 nucleotides in length, or 10-25 nucleotides in length, where the isolated oligonucleotide primers are capable of annealing under PCR conditions to a segment of a c-myc locus. According to example embodiments, the primer concentration should be optimized to the template concentration. A non-limiting example primer ratio is 250 nM of primers for a template concentration between 10 and 100 ng. According to example embodiments, the annealing temperature is about 56° C. and the extension time is about 30 seconds at 72° C., otherwise one may obtain non-specific products.

By way of non-limiting example, the isolated oligonucleotide primers may consist essentially of the above nucleotide sequences, i.e., SEQ ID NO: 1 or SEQ ID NO: 2. Nucleotide sequences "consisting essentially of" the listed sequences, are intended include the sequences themselves as well as sequences having at least 95%, 96%, 97%, 98% or 99% sequence identity therewith. Therefore, also provided are isolated oligonucleotide primers having a nucleotide sequence selected from SEQ ID NO: 1 or SEQ ID NO: 2 and sequences having at least 95%, 96%, 97%, 98% or 99% identity with such sequences.

Also provided is an isolated oligonucleotide consisting essentially of SEQ ID NO: 3, which includes sequences having at least 95%, 96%, 97%, 98%, or 99% identity with such sequences.

Further provided are systems and kits that include one or more components of a PCR stop assay, one or more components of a real time PCR assay, and one or more components to isolate genomic DNA. The systems and kits may be used for predicting cancer cell response to drug-based therapy. Example embodiments of such systems and kits may include for example primers for c-myc promoter as described. Non-limiting examples may include at least one isolated oligonucleotide primer consisting essentially of a nucleotide sequence selected from the group consisting of SEQ ID NO: 1 and SEQ ID NO: 2 (that is, including sequences having at least 95%, 96%, 97%, 98%, or 99% identity therewith). Non-limiting examples of components to isolate genomic DNA may include e.g., a genomic DNA isolation kit or a chromatin immunoprecipitation kit.

By way of non-limiting example, kits for predicting a response to drug-based therapy may include one or more components of a PCR-stop assay and a real time PCR assay; one or more components to isolate genomic DNA; and instructions on how to perform the PCR stop assay on cells that have been exposed to at least one drug, and instructions on how to quantify an amplified product using real time PCR to determine incidents of DNA breaks and therefore predict cell response to drug-based therapy.

Articles of manufacture, systems, and kits provided herein may additionally include reagents for carrying out the methods disclosed herein (e.g., buffers, Taq polymerase enzymes or any enzyme that amplifies DNA in a PCR reaction, cofactors, and agents to prevent contamination).

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

In this example, RKO colon cancer cells were treated with HDACi (Trichostatin A) followed by type II topoisomerase inhibitor (VP16) and vice-versa. In this experiment, cells were removed from a patient and then treated. The dose and time of HDACi treatments were selected to obtain enough histone acetylation to confer an open chromatin structure without triggering apoptosis or genome instability. In particular, in this experiment, 10 ng/ml TSA (HDACi) and 25 µM etoposide (topoisomerase II inhibitor) were used to treat cells for four and one hours respectively. With regard to example cancer cell treatment methods, see e.g., Kim, M. S., Blake, M., Baek, J. H., Kohlhagen, G., Pommier, Y. and Carrier, F. (2003) "Inhibition of histone deacetylase increases cytotoxicity to anticancer drugs targeting DNA." *Cancer Res*, 63, 7291-300.

Genomic DNA isolated from cells treated with TSA and VP16, individually and in combination, were used to quantitate type II topoisomerase mediated DNA breaks in c-myc p2 promoter.

Figure 2:
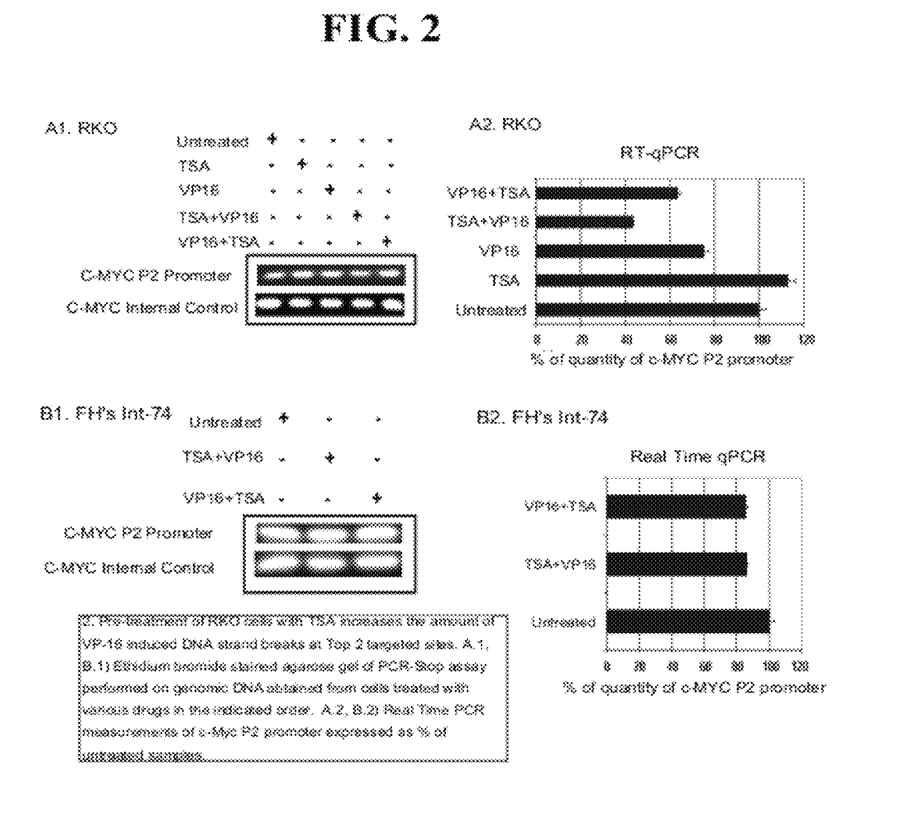

Results depicted in FIG. 2A1, FIG. 2B1, FIG. 2A2, and FIG. 2B2 clearly indicate that the HDACi (TSA) followed by type II topoisomerase inhibitor (VP16) treatment introduced a considerably higher percentage of breaks at c-myc locus compared to the reverse combination as well as the single drug treatments (see FIG. 2A2). FIG. 2A1 and FIG. B1 are a stained agarose gel of a PCR-Stop assay performed on genomic DNA obtained from cells (RKO—colon cancer cells in FIG. 2A1, and normal intestinal cells in FIG. 2B2) treated with various drugs. FIG. 2A2 and FIG. 2B2 are Real Time PCR measurements of c-myc P2 promoter expressed as a percentage of untreated samples. Together, FIGS. 2A1, 2B1, 2A2 and 2B2 show that pretreatment of RKO cancer cells with the HDACi Trichostatin A (TSA) increases topoisomerase inhibitor (VP16) strand breaks in the cancer cells (FIG. 2A1 and FIG. 2A2), as compared to normal intestinal cells that hardly respond to the drug combinations (FIG. 2B1 and FIG. 2B2.).

As can be seen in FIG. 2B2, normal intestinal cells have hardly responded to either of the drug combinations. These results indicate that the present methods could be used to assess the efficacy of the treatment as well as to determine the optimal dose, which could help reduce side effects associated with chemotherapy. For example, the present methods may be used to determine generally the types of cells that may be treated and/or an optimal dose for treatment of a type of cell. The present methods can also be used on individual patients to determine e.g., if that particular patient's cancer may be treated with a particular course of drugs and to determine an optimal dose for that patient.

Example 2

In this example, the PCR-Stop-Real Time-PCR technique was applied on the genomic DNA of two patients enrolled in a Phase 1 clinical trial (GCC0447) for Relapsed and/or refractory acute Leukemias and Myelodysplastic Syndromes. The trial was conduct at the Marlene and Stewart Greenebaum Cancer Center at the University of Maryland, Baltimore. The Principal Investigator was Dr. Douglas Ross.

Peripheral Blood Monoculear cells (PBMC) were obtained from the patients. Cells were obtained before treatment (A samples, see FIGS. 3A and 3C) and four hours after the last dose of HDACI (SAHA$^{Vorinostat}$) taken orally by each patient (400 mg) for three days (B samples, see FIGS. 3B and 3D). After collection, the cells were frozen in liquid nitrogen. The day prior to the assay, the cells were thawed and slowly diluted with cold media and spun at 800 rpm for 10 min. The cells were then re-suspended in fresh media (RPMI-10% FBS) and allowed to stabilize for 4 h at 37° C.

Figure 3A:
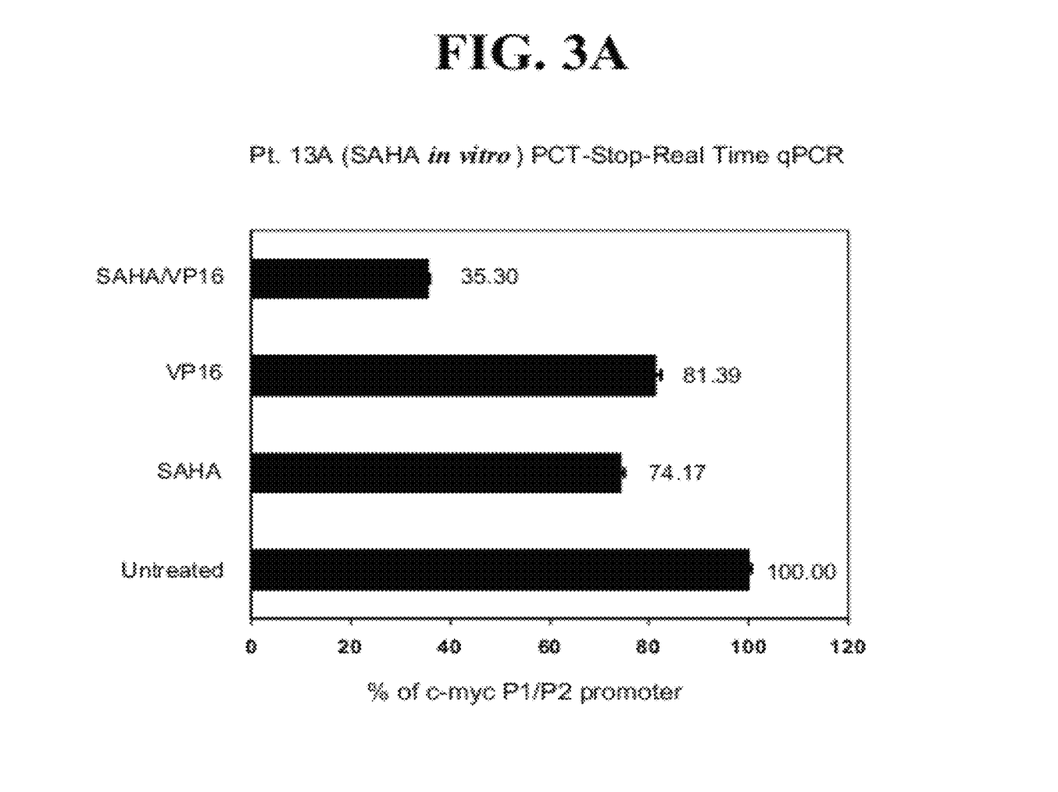
FIGS. 3A-3D depict the results of PCR-Stop-Real Time qPCR performed on Peripheral Blood Monoculear cells (PBMC) of two patients enrolled in a Phase 1 clinical trial for Relapsed and/or refractory acute Leukemias and Myelodysplastic Syndromes conducted at the Marlene and Stewart Greenebaum Cancer Center at the University of Maryland, Baltimore. The samples were obtained before (FIGS. 3A and 3C) and after SAHA treatment in vivo (FIGS. 3B and 3D). The FIG. 3A and FIG. 3C samples were treated in vitro with either SAHA (2.5 μM, 4 h), VP-16 (25 μM, 2 h) or SAHA followed by VP-16 (SAHA/VP16). The genomic DNA was extracted and 100 ng was assayed by PCR-Stop-RT-PCR as described herein. The FIG. 3B and FIG. 3D samples were collected from patients who received SAHA orally (400 mg) for three days and frozen. After equilibration the cells were either used as is (SAHA in vivo, FIGS. 3B and 3D) or treated in vitro with VP-16 (25 μM for 2 h). The genomic DNA was extracted and analyzed as described above.
Figure 3B:
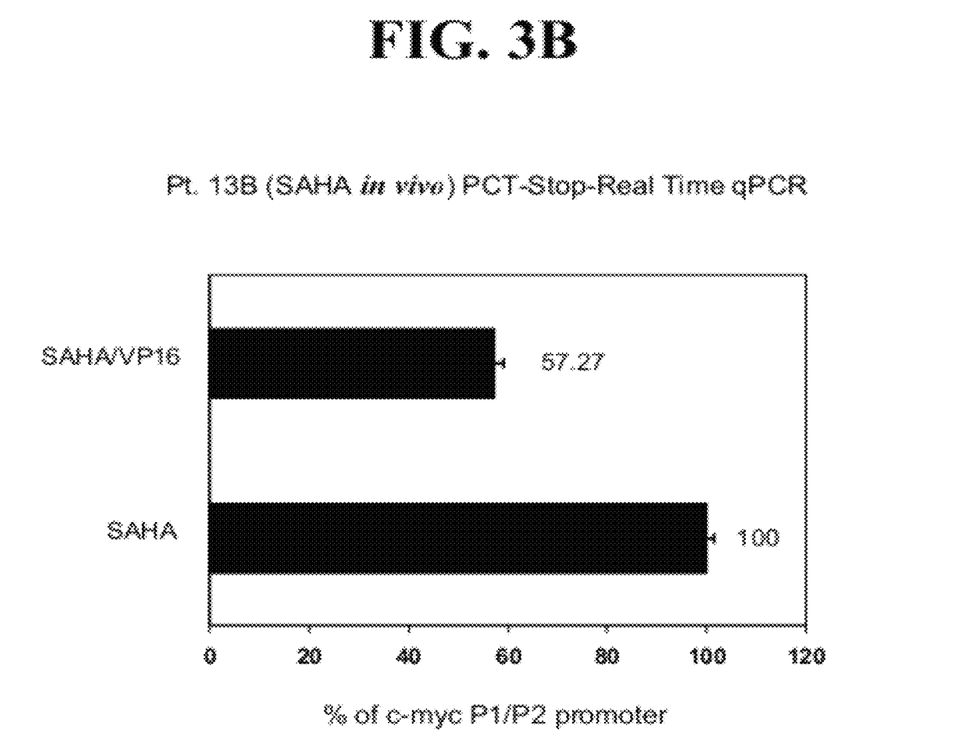
Figure 3C:
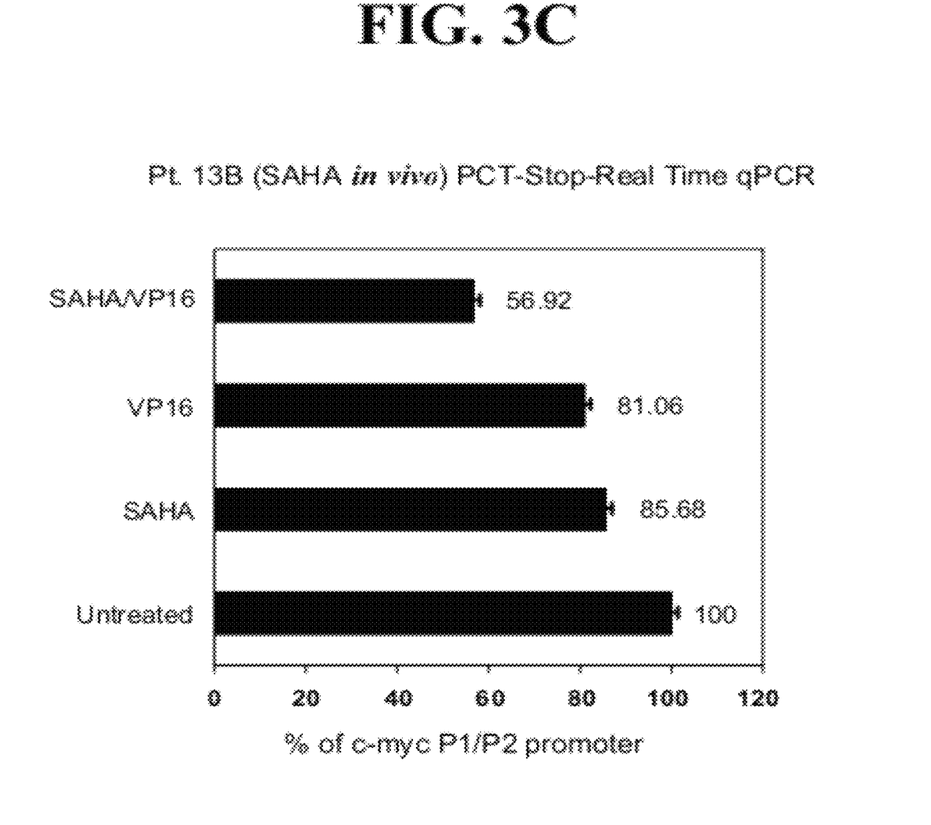
Figure 3D:
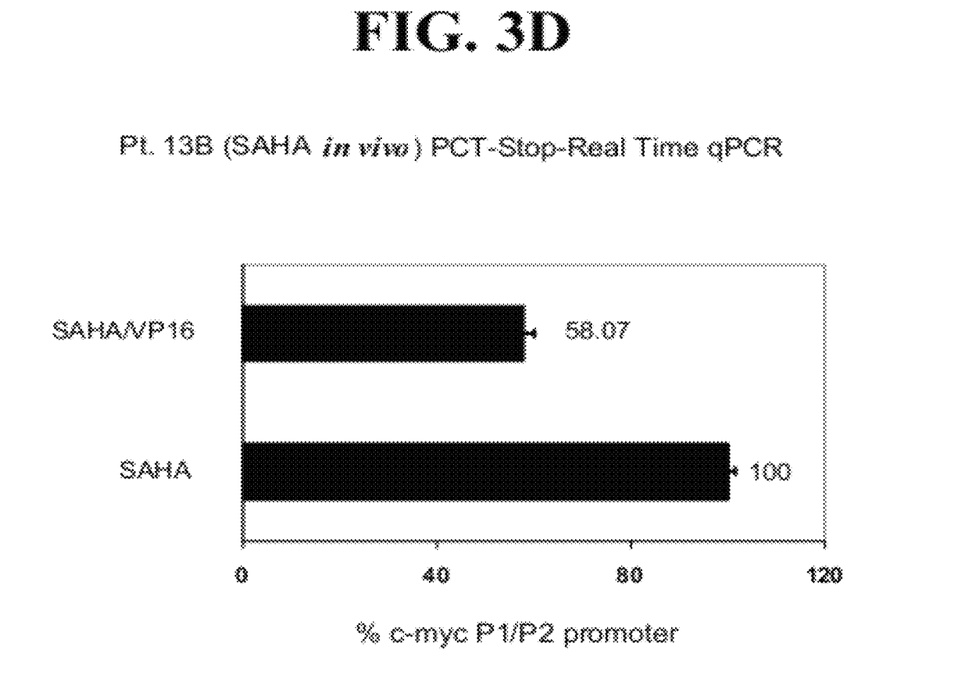

The A samples ($10 \times 10^6$ cells) were then treated in vitro with either SAHA (2.5 µg/ml, 4 h), VP-16 (25 µM, 2 h), or SAHA first followed by VP-16 (FIGS. 3A and 3C). The B samples were either used as is (SAHA in vivo) or treated with VP-16 for 2 h (FIGS. 3B and 3D). The cells were replenished with fresh media at the end of the treatments and genomic DNA (G&E Healthcare kit) was extracted 16 h later and assayed by PCR-Stop-Real Time qPCR as described in this application.

The data indicate that for both patients, cells pre-treated in vitro with SAHA are more sensitive to VP-16 induced DNA strand breaks than cells treated with VP-16 alone (FIG. 3A, FIG. 3C). Patient 13 (FIG. 3A) was the most sensitive with 45% more breaks occurring at the Top2 site when cells are pre-treated in vitro with SAHA. (See "SAHA/VP16" vs. "VP16" in FIG. 3A).

The data also indicate that in vivo administration of SAHA sensitizes the PBMC to VP-16 in a similar fashion in both patients with more than 40% more DNA strand breaks occurring at the Topo2 sites compared to SAHA alone. (See FIGS. 3B and 3D).

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of predicting a response to drug-based therapy comprising;
   exposing cancer cells to at least one Histone Deacetylase Inhibitor (HDACi) drug and thereafter at least one anticancer drug;
   mixing
   (i) DNA extracted from said cancer cells, and
   (ii) a primer pair comprising a forward primer and a reverse primer that target a c-myc promoter sequence, wherein at least one of the primers comprises an oligonucleotide primer having at least 95% identity to a nucleotide sequence selected from the group consisting of SEQ ID NO: 1 and SEQ ID NO: 2;
   amplifying the DNA in a PCR Stop assay, under conditions to allow production of an amplicon; and
   quantifying an amount of accumulated PCR amplified product using real time PCR, wherein the amount of PCR amplified product is inversely proportional to incidence of DNA breaks in an amplified region.

2. The method of claim 1, wherein the at least one HDACi is selected from the group consisting of hydroxamic acid, cyclic peptides, benzamide and short-chain fatty acids.

3. The method of claim 1, wherein the at least one HDACi is selected from the group consisting of trichostatin A (TSA), vorinostat (SAHA), sodium butyrate, phenylbutyrate, Valproic acid, Tributyrin, Depsipeptide, MS-275, CI994, and CBHA.

4. The method of claim 1, wherein the at least one anticancer drug comprises at least one drug selected from the group consisting of intra and inter cross-linking agents, Topoisomerase 1 inhibitors, Topoisomerase 2 inhibitors, alkylating agents, and antimetabolites.

5. The method of claim 1, wherein the at least one anticancer drug comprises at least one drug selected from the group consisting of etoposide (VP-16), Ara-C, ellipticine, doxorubicin, and cisplatin.

6. The method of claim 1, wherein the cancer cells comprise cancer cells selected from the group consisting of RKO (colon cancer) cells, MCF-7 (breast cancer) cells, U118 (glioblastoma) cells, and D54 (brain cancer) cells.

7. The method of claim 1, wherein the PCR amplified product is quantified using real time PCR by identifying a cycle number at which reporter dye emission intensities rise above background noise, where a higher cycle number corresponds to a higher incidence of DNA breaks.

8. The method of claim 7, wherein the reporter dye comprises an SYBR® green dye.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccctttataa tgcgagggtc t                                                21

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggctagggtg gaagagcc                                                    18

<210> SEQ ID NO 3
<211> LENGTH: 262
<212> TYPE: DNA
<213> ORGANISM: Homo sapiens

<400> SEQUENCE: 3
ccctttataa tgcgagggtc tggacggctg aggaccccg agctgtgctg ctcgcggccg        60
ccaccgccgg gccccggccg tccctggctc ccctcctgcc tcgagaaggg cagggcttct      120
cagaggcttg gcgggaaaaa gaacggaggg agggatcgcg ctgagtataa aagccggttt      180
tcggggcttt atctaactcg ctgtagtaat tccagcgaga ggcagaggga gcgagcgggc      240
ggccggctag ggtggaagag cc                                              262
```